(12) United States Patent
Fiering et al.

(10) Patent No.: US 8,679,313 B2
(45) Date of Patent: Mar. 25, 2014

(54) METHOD AND APPARATUS FOR CONCENTRATING MOLECULES

(75) Inventors: Jason O. Fiering, Boston, MA (US); Mark Keegan, Littleton, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 0 days.

(21) Appl. No.: 12/689,978

(22) Filed: Jan. 19, 2010

(65) Prior Publication Data

US 2010/0116657 A1 May 13, 2010

Related U.S. Application Data

(62) Division of application No. 11/729,046, filed on Mar. 28, 2007, now abandoned.

(51) Int. Cl.
*B01D 57/02* (2006.01)

(52) U.S. Cl.
USPC .......................................... 204/459; 204/548

(58) Field of Classification Search
USPC .......... 204/459, 518–548, 610; 422/502–508; 435/173.4–173.6, 446, 450
See application file for complete search history.

(56) References Cited

U.S. PATENT DOCUMENTS

| | | | |
|---|---|---|---|
| 1,583,051 A | 5/1926 | Kennedy | |
| 2,608,390 A | 8/1952 | Philippe | |
| 3,127,738 A | 4/1964 | Hasbrouck et al. | |
| 3,128,794 A | 4/1964 | Donald et al. | |
| 3,342,378 A | 9/1967 | Mezoff et al. | |
| 3,421,739 A | 1/1969 | Alberts et al. | |
| 3,470,912 A | 10/1969 | Bydal | |
| 3,506,244 A | 4/1970 | Strang | |
| 3,507,301 A | 4/1970 | Larson | |
| 3,510,240 A | 5/1970 | Rhinehart | |
| 3,847,773 A | 11/1974 | Snyder | |
| 3,852,013 A | 12/1974 | Upmeier | |
| 3,963,221 A | 6/1976 | Yi | |
| 4,214,610 A | 7/1980 | James et al. | |
| 4,222,671 A | 9/1980 | Gilmore | |
| 4,285,602 A | 8/1981 | Hagerty et al. | |
| 4,426,344 A | 1/1984 | Dinter et al. | |
| 4,465,582 A | 8/1984 | Richman | |
| 4,473,300 A | 9/1984 | Goins | |
| 4,518,260 A | 5/1985 | Goins | |

(Continued)

FOREIGN PATENT DOCUMENTS

| | | |
|---|---|---|
| DE | 3624626 A1 | 1/1988 |
| DE | 39 26 466 | 2/1991 |

(Continued)

OTHER PUBLICATIONS

Janasek et al. Electrostatic induction of the electric field into free-flow electrophoresis devices. Lab Chip, 6:710-13 (2006).

(Continued)

*Primary Examiner* — Susan D Leong
(74) *Attorney, Agent, or Firm* — Foley & Lardner LLP; Edward A. Gordon

(57) ABSTRACT

A method and apparatus for continuously separating or concentrating molecules that includes flowing two fluids in laminar flow through an electrical field and capturing at one of three outputs a fluid stream having a different concentration of molecules.

14 Claims, 11 Drawing Sheets

(56) References Cited

U.S. PATENT DOCUMENTS

| | | | |
|---|---|---|---|
| 4,553,849 A | 11/1985 | Goins | |
| 4,948,481 A | 8/1990 | Mullner | |
| 4,983,038 A | 1/1991 | Ohki et al. | |
| 5,094,788 A | 3/1992 | Schrenk et al. | |
| 5,180,480 A * | 1/1993 | Manz | 204/644 |
| 5,185,071 A | 2/1993 | Serwer et al. | |
| 5,250,188 A | 10/1993 | Bruening et al. | |
| 5,269,995 A | 12/1993 | Ramanathan et al. | |
| 5,275,706 A | 1/1994 | Weber | |
| 5,518,311 A | 5/1996 | Althaus et al. | |
| 5,531,831 A | 7/1996 | Sweeney et al. | |
| 5,620,714 A | 4/1997 | Veen | |
| 5,765,373 A | 6/1998 | Bittle et al. | |
| 5,780,067 A | 7/1998 | Herrington, Jr. | |
| 5,803,600 A | 9/1998 | Schubert et al. | |
| 5,816,045 A | 10/1998 | Blocker et al. | |
| 5,824,204 A | 10/1998 | Jerman | |
| 5,826,981 A | 10/1998 | Fowler et al. | |
| 5,904,424 A | 5/1999 | Schwesinger et al. | |
| 5,932,100 A | 8/1999 | Yager et al. | |
| 6,082,891 A | 7/2000 | Schubert et al. | |
| 6,136,171 A | 10/2000 | Frazier et al. | |
| 6,136,272 A | 10/2000 | Weigl et al. | |
| 6,143,152 A | 11/2000 | Simpson et al. | |
| 6,190,034 B1 | 2/2001 | Nielsen et al. | |
| 6,221,677 B1 | 4/2001 | Wu et al. | |
| 6,225,497 B1 | 5/2001 | Becker et al. | |
| 6,264,900 B1 | 7/2001 | Schubert et al. | |
| 6,299,657 B1 | 10/2001 | Schubert et al. | |
| 6,321,998 B1 | 11/2001 | Schubert et al. | |
| 6,328,868 B1 | 12/2001 | Weber | |
| 6,387,707 B1 | 5/2002 | Seul et al. | |
| 6,432,630 B1 * | 8/2002 | Blankenstein | 435/4 |
| 6,454,945 B1 | 9/2002 | Weigl et al. | |
| 6,467,503 B2 | 10/2002 | Schlesch et al. | |
| 6,479,734 B2 | 11/2002 | Iba et al. | |
| 6,623,860 B2 | 9/2003 | Hu et al. | |
| 6,676,835 B2 | 1/2004 | O'Connor et al. | |
| 6,692,627 B1 | 2/2004 | Russell et al. | |
| 6,695,147 B1 | 2/2004 | Yager et al. | |
| 6,705,357 B2 | 3/2004 | Jeon et al. | |
| 6,802,640 B2 | 10/2004 | Schubert et al. | |
| 6,845,787 B2 | 1/2005 | Karp et al. | |
| 6,851,846 B2 | 2/2005 | Fujii et al. | |
| 6,877,892 B2 | 4/2005 | Karp | |
| 6,890,093 B2 | 5/2005 | Karp et al. | |
| 6,905,324 B2 | 6/2005 | Cloeren | |
| 6,923,907 B2 | 8/2005 | Hobbs et al. | |
| 6,935,772 B2 | 8/2005 | Karp et al. | |
| 6,958,245 B2 | 10/2005 | Seul et al. | |
| 6,981,522 B2 | 1/2006 | O'Connor et al. | |
| 7,005,050 B2 | 2/2006 | Burns et al. | |
| 7,033,473 B2 | 4/2006 | Gascoyne et al. | |
| 7,056,746 B2 | 6/2006 | Seul et al. | |
| 7,077,906 B2 | 7/2006 | Colombo et al. | |
| 7,100,636 B2 | 9/2006 | King | |
| 7,135,144 B2 | 11/2006 | Christel et al. | |
| 7,138,269 B2 | 11/2006 | Blankenstein | |
| 7,258,774 B2 | 8/2007 | Chou et al. | |
| 7,261,812 B1 | 8/2007 | Karp et al. | |
| 7,316,503 B2 | 1/2008 | Mathys et al. | |
| 7,472,794 B2 | 1/2009 | Oakey et al. | |
| 7,487,799 B2 | 2/2009 | Wobben | |
| 7,520,661 B1 | 4/2009 | Lawson | |
| 7,632,405 B2 | 12/2009 | Siddiqi | |
| 7,699,767 B2 | 4/2010 | Mueth et al. | |
| 2002/0045738 A1 * | 4/2002 | Singh et al. | 536/23.1 |
| 2002/0057627 A1 | 5/2002 | Schubert et al. | |
| 2002/0187503 A1 | 12/2002 | Harrold et al. | |
| 2003/0057092 A1 | 3/2003 | Chien et al. | |
| 2004/0092033 A1 | 5/2004 | Gustafson et al. | |
| 2004/0182707 A1 | 9/2004 | Jardemark et al. | |
| 2004/0256230 A1 | 12/2004 | Yager et al. | |
| 2004/0257907 A1 | 12/2004 | Xu et al. | |
| 2005/0011761 A1 * | 1/2005 | Chien et al. | 204/450 |
| 2005/0061669 A1 | 3/2005 | Woudenberg et al. | |
| 2005/0178701 A1 | 8/2005 | Roth et al. | |
| 2008/0067068 A1 | 3/2008 | Li | |
| 2008/0237044 A1 | 10/2008 | Fiering et al. | |
| 2009/0044619 A1 | 2/2009 | Fiering et al. | |
| 2009/0078614 A1 | 3/2009 | Varghese et al. | |
| 2009/0086572 A1 | 4/2009 | Miyoshi et al. | |

FOREIGN PATENT DOCUMENTS

| | | |
|---|---|---|
| DE | 3926466 | 2/1991 |
| DE | 19748481 | 5/1999 |
| EP | 0 434 556 | 6/1991 |
| EP | 0 434 556 A1 | 6/1991 |
| EP | 1 742 057 | 1/2007 |
| WO | WO-96/26782 | 9/1996 |
| WO | WO-96/26782 A1 | 9/1996 |
| WO | WO-01/87458 | 11/2001 |
| WO | WO-01/87458 A1 | 11/2001 |
| WO | WO-2009/023507 | 2/2009 |
| WO | WO-2009/023507 A2 | 2/2009 |

OTHER PUBLICATIONS

Kamholz et al. Quantitative Analysis of Molecular Interaction in a Microfluidic Channel: The T-Sensor. Anal. Chem., 71:5340-47 (1999).

Krivankova et al. Continuous free-flow electrophoresis. Electrophoresis, 19:1064-74 (1998).

Osbourn et al. On-line preconcentration methods for capillary electrophoresis. Electrophoresis, 21:2768-79 (2000).

Li et al. Rapid and sensitive separation of trace level protein digests using microfabricated devices coupled to a quadrupole time-of-flight mass spectrometer. Electrophoresis 2000. 21:198-210 (2000).

Jung et al. Thousandfold signal increase using field-amplified sample stacking for on-chip eletrophoresis. Electrophoresis 2003. 24:3476-83 (2003).

Gale et al. A Micromachined Electrical Field-Flow Fractionation (µ-EFFF) System. IEEE Transactions on Biomedical Engineering. 45:12(1459-69 (Dec. 1998).

Ismagilov et al. Experimental and theoretical scaling laws for transverse diffusive broadening in two-phase laminar flows in microchannels. App. Phys. Lett. 76(17): 2376-78. (2000).

Song et al. Continuous-Flow pI-Based Sorting of Proteins and Peptides in a Microfluidic Chip Using Diffusion Potential. Anal. Chem. 78:11, 3528-36. (2006).

Welte et al. Structure and Function of the Porin Channel. Kidney International, 48:930-940 (1995).

Blankenstein. Microfabricated Flow system for magnetic cell and particle separation. Scientific and Clinical Applications of magnetic carriers, Ch. 16, pp. 223-245 (1997).

Wang et al. "An Overlapping Crisscross Micromixer Using Chaotic Mixing Principles." J. Micromech. Microeng. 16, 2684-91. (2006).

Chen et al, "Topologic Mixing on a Microfludic Chip," App. Phys. Ltrs. 84:12, 2193-95. )2-4).

Fiering et al., "Continuous Hihg-Throughput Magnetic Seperation of Pathogens from Blood," Micro-Fludic Components and Systems, 0345. (2008).

Albrecht et al. Rapid Free Flow Isoelectric Focusing via Novel Electrode Structures. 9th Intl. Conf. on Miniaturized Systems for Chemistry and Life Sciences (MicroTAS). (2005).

Biscans et al. Influence on flow and diffusion on protein separation in a continuous flow electrophoresis cell: Computation procedure. Electrophoresis, 9:84-89 (1988).

Blankenstein "Microfabricated Flow system for magnetic cell and particle separation" Scientific and Clinical Applications of magnetics carriers. 1997, Chapter 16, pp. 223-245.

Chen et al. "Topologic Mixing on a Microfluidic Chip." App. Phys. Ltrs. 84:12, 2193-95. (2004).

Chen, et al. Magnetic separation of micro-spheres from viscous biological fluids, Phys. Med. Biol. 52 (2007) 1185-1196.

Chien, R.L. Sample stacking revisited: A personal perspective. Electrophoresis, 24:486-97 (2003).

(56) References Cited

OTHER PUBLICATIONS

Clifton et al. Conditions for purification proteins by free-flow zone electrophoresis. Electrophoresis, 11:913-19 (1990).
Edwards et al. A Microfabricated Thermal Field-Flow Fractionation System. Anal. Chem. 74:6, 2322-26 (2002).
Fiering et al. "Continuous High-Throughput Magnetic Separation of Pathogens from Blood." Micro-Fluidic Components and Systems, 0345. (2008).
Furdui, et al. Immunomagnetic T cell capture from blood for PCR analysis using microfluidic systems, Miniaturisation for Chemistry, Biology & Bioengineering, The Royal Society of Chemistry, Lab chip (2004) 4, 614-618.
Gale et al. A Micromachined Electrical Field-Flow Fractionation (μ-EFFF) System. IEEE Transactions on Biomedical Engineering. 45:12 (1459-69 (Dec. 11, 1998).
Han, et al. Continuous magnetophoretic separation of blood cells in microdevice format, Journal of Applied Physics, vol. 96, No. 10, Nov. 15, 2004.
Han, et al. Microsystems for isolation and electrophysiological analysis of breast cancer cells from blood, Biosensors and Bioelectronics 21 (2006) 1907-1914.
Han, et al. Paramagnetic capture mode magnetophoretic microseparator for high efficiency blood cell separations, The Royal Society of Chemistry, Lal Chip (2006) 6, 265-273.
Hoffman et al. A Novel Repulsive-Mode High Gradient Magnetic—I. Design and Experimental Results, IEEE Transactions on Magnetics, vol. 40, No. 2, Mar. 2004.
Hoffman et al. Continuous free-flow electrophoresis separation of cytosolic proteins from the human colon carcinoma cell line LIM 1215: A non two-dimensional gel electrophoresis-based proteome analysis strategy. Proteomics, 1:807-18 (2001).
Huang et al. On-line isotachophoretic preconcentration and gel electrophoretic separation on sodium dodecyl sulfate-proteins on a microchip. Electrophoresis, 26:2254-60 (2005).
Huber et al. Programmed Adsorption and Release of Proteins in a Microfluidic Device. Science. 301:352-54 (Jul. 18, 2003).
Inglis, et al. Continuous microfluidic immunomagnetic cell separation, Applied Physics Letters, vol. 85, No. 21, Nov. 22, 2004.
International Search Report and Written Opinion mailed Oct. 8, 2008 in PCT Application No. PCT/US2008/005002 (8 pages).
International Search Report and Written Opinion mailed Oct. 9, 2008 in PCT Application No. PCT/US2008/003532 (7 pages).
Irmia et al. "Universal Microfluidic Gradient Generator." Anal. Chem. 78, 3472-77. (2006).
Ismagilov et al. "Pressure-Driven Laminar Flow in Tangenetial Microchannels: an Elastomeric Microfluidic Switch." Anal. Chem. (2001).
Ismagilov et al. Experimental and theoretical scaling laws for transverse diffusive broadening in two-phase laminar flows in microchannels. Ann. Phys. Lett. 76(17): 2376-78. (2000).
Jacobson et al. Microchip electrophoresis with sample stacking. Electrophoresis, 16:481-86 (1995).
Janasek et al. Electrostatic induction of the electric field into free-flow electrophoresis devices. Lab Chip, 6:7.10-13 (2006).
Jung et al. Thousandfold signal increase using field-amplified sample stacking for on-chip electrophoresis. Electrophoresis 2003. 24:3476-83 (2003).
Kamholz et al. Quantitative Analysis of Molecular Interaction in a Microfluidic Channel: The T-Sensor. Anal. Chem., 71 :5340-47 (1999).
Kohlheyer et al. Free-flow zone electrophoresis and isoelectric focusing using a microfabricated glass device with ion permeable membranes. Lab Chip, 6:374-80 (2006).
Krivankova et al. Continuous free-flow electrophoresis. Electrophoresis 19:1064-74 (1998).
Lao et al. Miniaturized Flow Fractionation Device Assisted by a Pulsed Electric Field for Nanoparticle Separation. Anal. Chem. 74:20, 5364-69 (2002).

Li et al. Rapid and sensitive separation of trace level protein digests using microfabricated devices coupled to a quadruple time-of-flight mass spectrometer. Electrophoresis 2000. 21:198-210 (2000).
Lien, et al. Purification and enrichment of virus samples utilizing magnetic microfluidic system, The Royal Society of Chemistry, Lab Chip (2007) 7, 868-875.
Millipore. Urine Concentration with Amicon Ultra Centrifugal Filters. Downloaded from http://www.millipore.com/publications.nsf/docs/6djsf9. (2005).
Notice of Allowance issued Jun. 19, 2012 in U.S. Appl. No. 12/105,805 (10 pages).
Office Action issued Mar. 22, 2012 in U.S. Appl. No. 12/105,805 (10 pages).
Office Action issued Jan. 5, 2011 in U.S. Appl. No. 12/105,805 (9 pages).
Office Action issued Oct. 16, 2009 in U.S. Appl. No. 11/729,046 (38 pages).
Office Action issued Sep. 23, 2011 in U.S. Appl. No. 12/105,805 (12 pages).
Olesen, et al. Quantitative characterization of magnetic separators: Comparison of systems with and without integrated microfluidic mixers, Biomed Microdevices (2007) 9:195-205.
Osbourn et al. On-line preconcentration methods for capillary electrophoresis. Electrophoresis, 21 :2768-79 (2000).
Pamme, et al. Continuous sorting of magnetic cells via on-chip free-flow magnetophoresis, The Royal Society of Chemistry, Lab Chip (2006) 6, 974-980.
Pamme, et al. On-Chip Free-Flow Magnetophoresis: Continuous Flow Separation of Magnetic Particles and Agglomerates, Anal. Chem. (2004) 76, 7250-7256.
Quirino et al. Approaching a Million-Fold Sensitivity Increase in Capillary Electrophoresis with Direct Ultraviolet Detection: Cation-Selective Exhaustive Injection and Sweeping. Anal. Chem., 72:1023-30 (2000).
Raymond et al. Continuous Sample Preparation Using Free-Flow Electrophoresis on a Silicon Microstructure. Transducers '95, Eurosensors IX, The 8th International Conference on Solid-State Sensors and Actuators, and Eurosensors IX, Stockholm, Sweden, Jun. 25-29, 1995, pp. 760-763.
Raymond et al. Continuous Sample Pretreatment Using a Free-Flow Electrophoresis Device Integrated onto a Silicon Chip. Anal. Chem., 66:2858-65 (1994).
Reyes et al. Micro Total Analysis Systems. 1. Introduction, Theory, and Technology. Anal. Chem., 74:2623-36 (2002).
Ross et al. Microfluidic Temperature Gradient Focusing. Anal. Chem., 74:2556-64 (2002).
Song et al. Electrophoretic Concentration of Proteins at Laser-Patterned Nanoporous Membranes in Microchips. Anal. Chem., 76:4589-92 (2004).
Song et al., "Continuous-Flow pI-Based Sorting of Proteins and Peptides in a Microfluidic Chip Using Diffusion Potential", Anal. Chem. 78:11, 3528-36 (2006).
Sun, et al. Continuous, Flow-Through Immunomagnetic Cell Sorting in a Quadrupole Field, Cytometry 33: 469-475 (1998).
Takayasu, et al. Continuous Magnetic Separation of Blood Components from Whole Blood, IEEE Transactions on Applied Superconductivity, vol. 10, No. 1, Mar. 1, 2000.
Toner, et al. Blood-on-a-Chip, Annu. Rev. Biomed. Eng. (2005) 7:77-103.
Wainright et al. Sample pre-concentration by isotachophoresis in microfluidic devices. Journal of Chromatography A, 979:69-80 (2002).
Wang et al. "An Overlapping Crisscross Micromixer Using Chaotic Mixing Principles." J. Micromech. Microenq. 16, 2684-91. (2006).
Wang et al. Million-fold Preconcentration of Proteins and Peptides by Nanofluidic Filter. Anal. Chem., 77:4293-99 (2005).
Wang et al. Two-Dimensional Protein Separation with Advanced Sample and Buffer Isolation Using Microfluidic Valves. Anal. Chem., 76:4426-31 (2004).

(56) References Cited

OTHER PUBLICATIONS

Welte et al. Structure and Function of the Porin Channel. Kidney International, 48:930-40 (1995).

Xia et al. "Chaotic Micromixers Using Two-Layer Crossing Channels to Exhibit Fast Mixing at Low Reynolds Numbers." Royal Soc. of Chem., Lab Chip, 5, 748-55. (2005).

Xia, et al. Combined microfluidic-micromagnetic separation of living cells in continuous flow. Biomed Microdevices (2006) 8:299-308.

Zhang et al. High-Speed Free-Flow Electrophoresis on Chip. Anal. Chem., 75:5759-66 (2003).

* cited by examiner

METHOD AND APPARATUS FOR CONCENTRATING MOLECULES

REFERENCE TO RELATED APPLICATION

This application is a divisional of U.S. patent application Ser. No. 11/729,046 entitled "Method and Apparatus for Concentrating Molecules" filed on Mar. 28, 2007, the entire contents of which are hereby incorporated by reference.

FIELD OF INVENTION

The invention relates generally to a method and apparatus for continuous separation or concentration of proteins (or other biological molecules) from aqueous solutions in a flow-through configuration.

BACKGROUND OF THE INVENTION

In analytical chemistry, electrophoresis refers to methods that use electric fields to manipulate and separate charged molecules in solution. Capillary electrophoresis (CE) refers to a family of "traditional" techniques where the sample is loaded into a capillary and its components are separated into bands along the axial direction. The separation arises whenever components of the sample have unique electrophoretic mobility. These bands can be detected, for example, by a fixed optical system as they flow past. The apparatus may be relatively simple since high voltage electrodes at each end of the capillary serve to not only separate the sample but also to inject the sample into the capillary by taking advantage of electroosmotic flow. The art of CE involves identifying appropriate parameters, buffers, and additives for each specific analyte to maximize separation and resolution between bands The limits of resolution in CE are partly determined by diffusion of separated analyte into the surrounding buffer, which broadens the bands. Two methods of countering this effect are called focusing and stacking. The object of stacking is to compress the sample molecules into a narrow band, prior to performing the separation, so that differences in mobility are made more distinct. One kind of stacking is achieved by using electrophoresis to drive molecules against an interface between two solutions of differing conductivity. If the sample is in a low-conductivity buffer, electric field strength across it will be high, and electrophoretic velocity will be high. When the sample ions reach a transition to a high-conductivity buffer, electric field strength will drop, as will their velocity, and they will collect at the interface. However, this technique is limited to batch processing. A need exists in the art for a method and apparatus for continuously separating or concentrating molecules using stacking. So-called "free flow electrophoresis" is another technique known in the art that permits continuous separations, but it is not conventionally used with stacking.

SUMMARY OF THE INVENTION

The invention addresses the deficiencies in the prior art by using a free flow electrophoresis configuration in conjunction with discontinuous buffers to achieve bulk concentration of molecules.

In one aspect, the invention relates to a device for separating or concentrating molecules. The device includes a microfabricated flow channel having an upstream end and a downstream end. At the upstream end, the channel includes two input ports. One input port introduces into the channel a low-conductivity fluid stream containing a target molecule and potentially other molecules. The other input port introduces into the flow channel a high-conductivity fluid stream. The channel includes three outlet ports. One outlet port receives most of the low-conductivity fluid stream. A second output port receives most of the high-conductivity fluid stream. A third output port is located around the center of the end of the channel. This port receives a mix of both fluid streams. The device also includes a pair of electrodes, one on each side of the channel. When voltage is applied, the electrodes will create an electric field across the channel.

In one embodiment, an electrode interface includes an opening in the channel adjacent to a fluid stream. The opening is separated from a reservoir by an ion-permeable barrier, which permits ions to pass but does not permit bulk fluid flow. The reservoir interfaces with an external electrode. The external electrode can be electrically connected to an external power source for applying a voltage of various polarities and magnitudes to the electrode. When voltage is applied to both electrodes, an electric field forms across the width of the channel.

In one embodiment, the device is molded into a substrate. In another embodiment, the device is etched into a substrate.

In one embodiment, the device is approximately 5 mm wide, 10 μm to 100 μm deep, and about 2.3 cm to about 5 cm long.

In one embodiment, the device includes a third input port at the upstream end. In such an embodiment, the sample fluid and the low-conductivity buffer are introduced from separate input ports.

In another aspect, the invention relates to a device for separating or concentrating molecules. The device includes a channel, two input ports, and three output ports, like the device described above. In addition, the device also includes integrated electrodes. The electrodes are positioned proximate to the channel.

In one embodiment, the electrodes are separated from the channel by ion-permeable barriers.

In one embodiment, the ion-permeable barriers are comprised of arrays of smaller channels.

In one embodiment, the device includes a power source for applying voltage to the electrodes and controls for controlling the strength and polarity of voltage applied to the electrodes.

In another aspect, the invention relates to a method for separating or concentrating molecules. The method includes selecting the pH of the low-conductivity buffer so that the charge of the target molecule is non-zero, flowing the low-conductivity buffer, with sample, and the high-conductivity buffer through the channel in laminar flow, applying an electric field with appropriate polarity and strength to cause the target molecule to accumulate at the interface between the two fluids, and collecting portions of both fluid streams at the interface between the two fluids at the end of the channel.

BRIEF DESCRIPTION OF THE FIGURES

The foregoing discussion will be understood more readily from the following detailed description of the invention with reference to the following drawings.

DESCRIPTION OF CERTAIN ILLUSTRATIVE EMBODIMENTS

Figure 1:
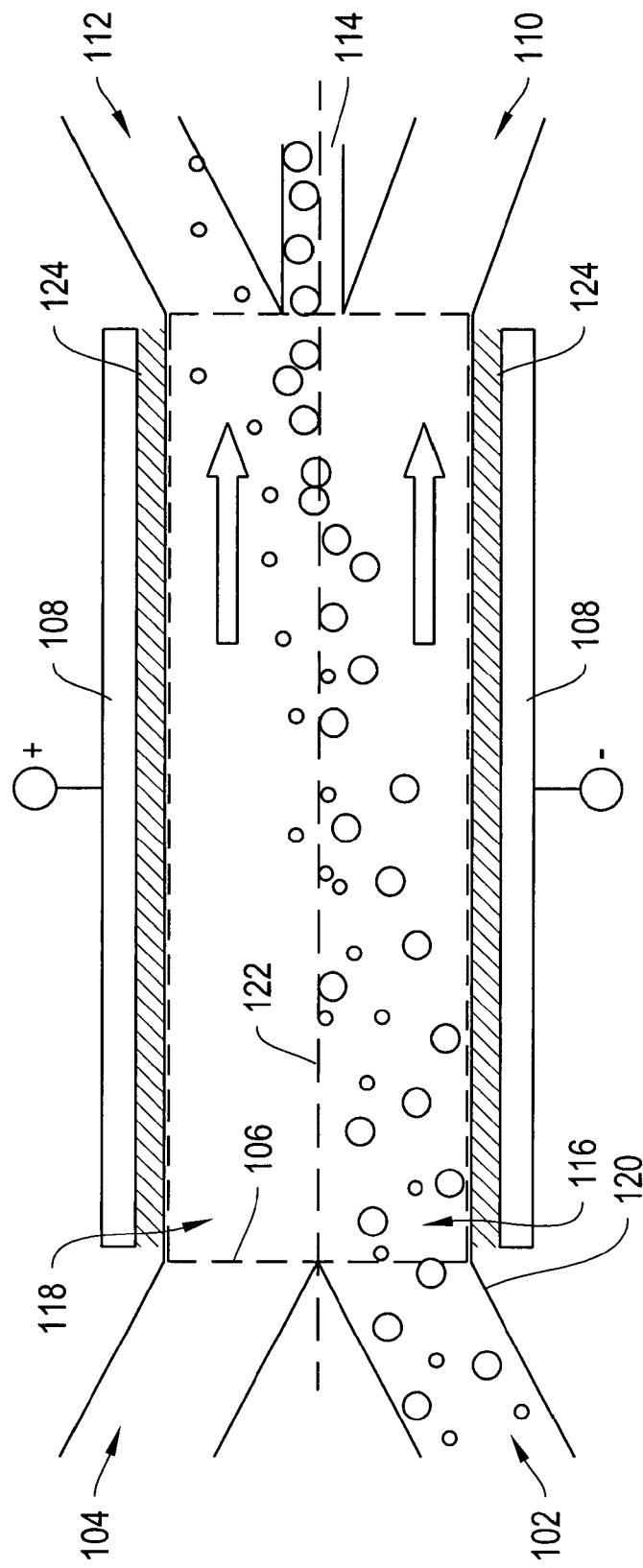
FIG. 1 is a schematic diagram of a device for concentrating molecules into an output stream with a higher concentration than the input stream.

FIG. 1 depicts a schematic diagram of a device for concentrating molecules into an output stream with a higher concentration than the input stream. The device 100 includes a sample input port 102, a buffer input port 104, a flow channel 106, a pair of electrodes 108, a sample output port 110, a buffer output port 112, and a target output port 114.

The input ports 102 and 104 are positioned to introduce two fluid streams into the flow channel in laminar flow. The sample input port 102 introduces a fluid stream having a target molecule in it 116. The buffer input port 104 introduces a fluid stream 118 having a conductivity that is substantially different than the fluid stream 116 introduced through the sample input port 102.

The width and depth of the flow channel 106 are selected to allow the fluid streams from the two inputs 102 and 104 to be in laminar flow through the flow channel 106. For example, the flow channel may be 0.5 mm to 5 mm wide and 10 μm to 100 μm deep. The length of the channel 106 is selected to be sufficiently long to allow the target molecules to have sufficient time to travel from one wall 120 of the flow channel to about the interface 122 between the two fluids. For example, in various embodiments the channel is between about 2.3 cm long to about 5 cm long, though shorter or longer flow channels may also be suitable.

The pair of electrodes 108 are separated from the flow channel 106 by a pair of electrode interfaces 124. Each electrode interface 124 includes an ion-permeable barrier that permits the flow of electrical current between the electrodes 108 as ion transport across the barrier without permitting bulk fluid flow. By applying voltage to the electrodes 108, an electric field is established transverse to the flow channel 106.

As the fluids 116 and 118 flow through the flow channel 106, the electric field causes molecules to move towards the interface 122 of the two fluid streams. The polarity of the field is selected based upon the charge of the target molecule. The polarity is selected to cause the target molecule to move towards the interface 122 of the two fluid streams. The strength of the electric field is selected based upon the charge of the target molecule and the flow rate of the fluid streams through the flow channel 106. For example, in various embodiments, the field strength is between about 200 V/cm to about 1000 V/cm.

Figure 6:
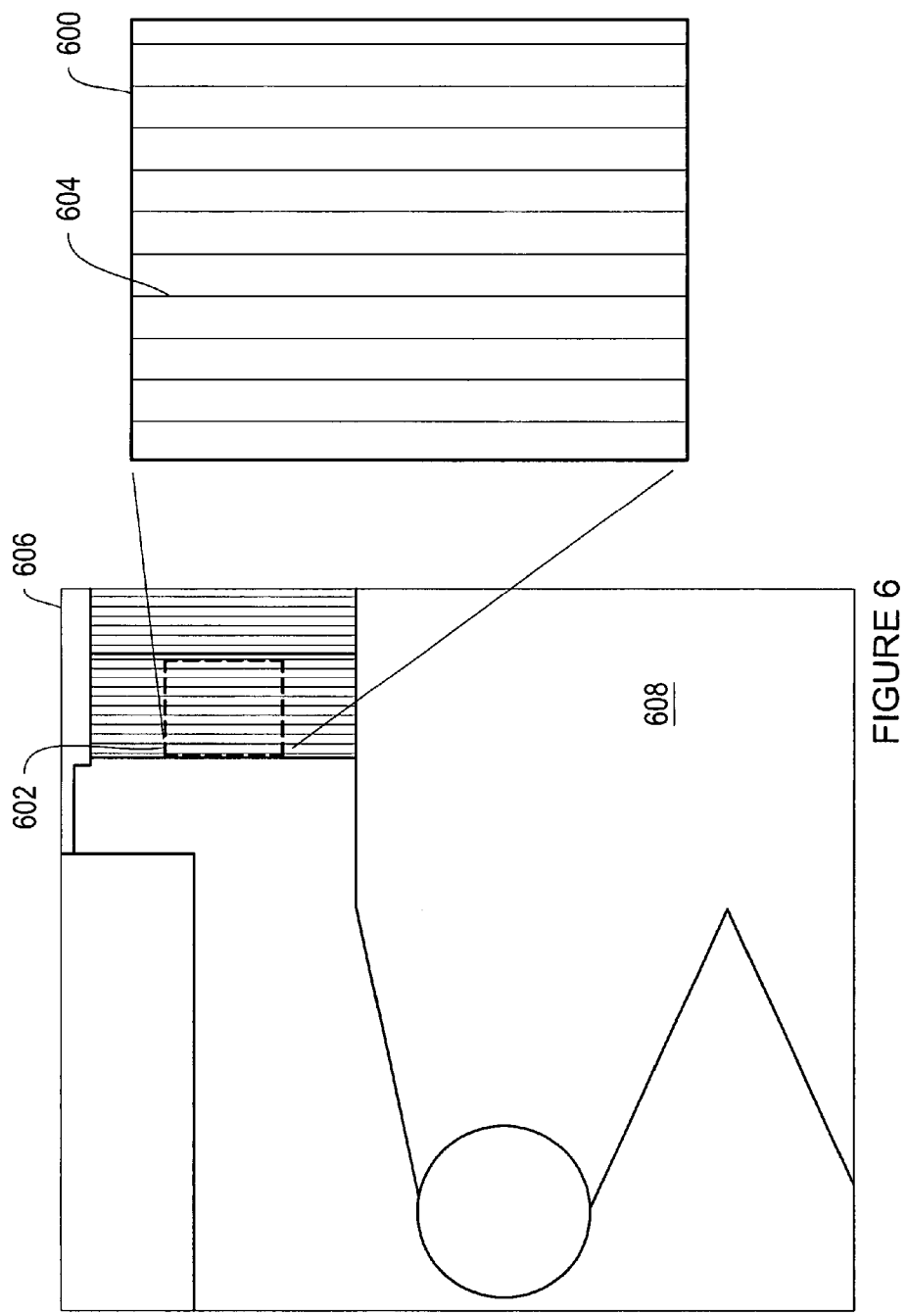
FIG. 6 is a drawing illustrating a close-up view of the ion-permeable barrier comprised of an array of channel

Preferably, the electrode interface 124 includes an array of channels, as described further in FIG. 6. In other embodiments, the electrode interface 124 includes hydrodynamic resistance channels, gels polymerized in situ, packed bed materials that are themselves loaded through microfluidic delivery, covered electrodes where steady fluid flow removes gas bubbles, or insulated electrodes where flow rates are sufficient to sweep away screening charges.

In one embodiment, the electrode interfaces 124 electrically couple the flow channel 106 to electrodes integrated into the device. For example, the electrode may be formed on the substrate on which the channel is formed. In other embodiments, the electrode interfaces 124 electrically couple the flow channel 106 to external electrodes, as described further in FIG. 3.

Because of the difference in conductivities between the two fluids 116 and 118, the electric field across the first fluid stream 116 is higher than the electric field across the second fluid stream 118. Once molecules from the first fluid stream 116 traverse the interface 122 between the first fluid stream 116 and the second fluid stream 118, they experience the weaker electric field of the second fluid stream 118. Because the electric field is weaker, the velocity of a molecule slows, resulting in an accumulation of molecules at about the interface 122 between the two fluids 116 and 118.

At the downstream end of the channel 106 are a sample output port 110, a buffer output port 112, and a target output port 114. The sample output port 110 collects most of the first fluid stream 116. The buffer output port collects most of the second fluid stream 118. The target output port 114 is located at about the interface 122 between the two fluid streams 116 and 118. As the fluids flow down the flow channel 106, the molecules accumulate at the interface 122 between the two fluids. Because the target output port 114 is positioned at about that interface 122, when the fluids 116 and 118 reach the end of the channel, the fluid containing those molecules continues flowing into the target output port 114. The target output port 114 therefore collects the target molecules from the first fluid 116. It is sized, however, to collect a smaller volume of fluid than the fluid streams 116 and 118 than the output ports. The increased concentration of target molecules in the fluid collected at the target output port is higher than in the first fluid stream 116.

Figure 2:
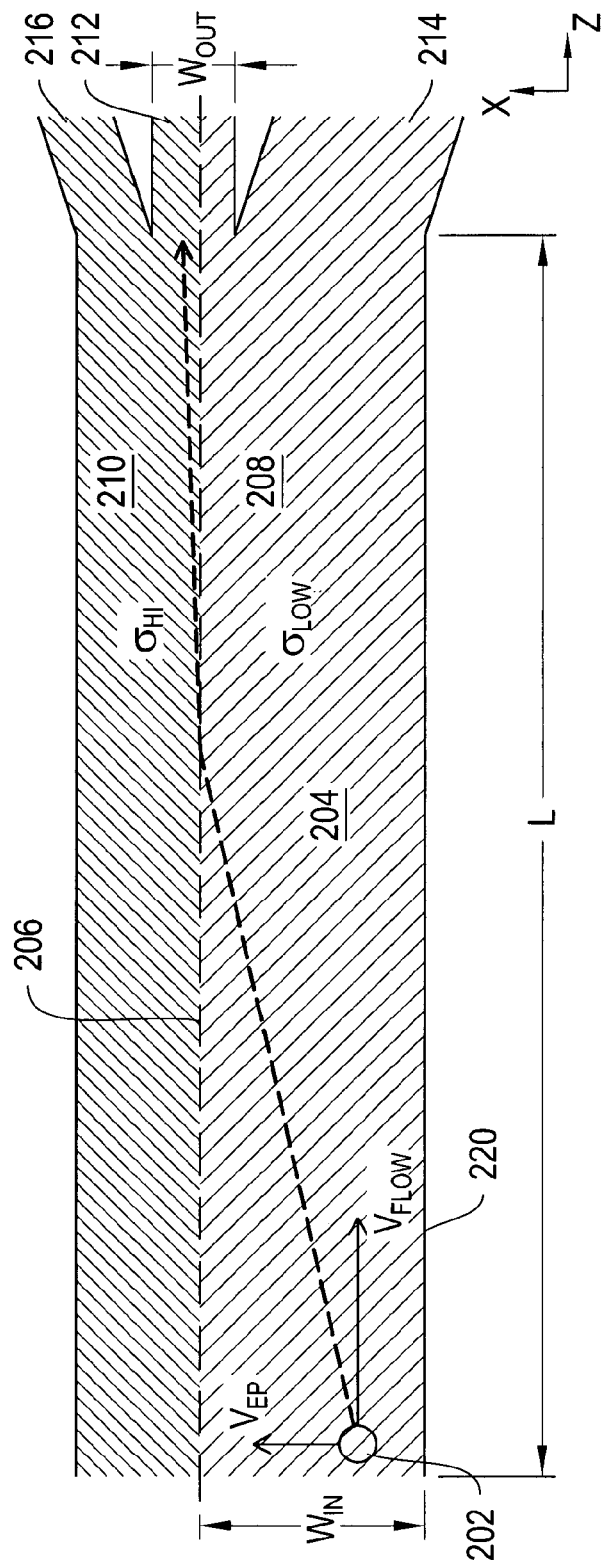
FIG. 2 is a schematic diagram illustrating the trajectory of a molecule in the invention subject to pressure driven flow and a transverse electric field.

FIG. 2 depicts the trajectory of a molecule 202 in a channel 204 of a molecule concentrator device subject to pressure driven flow and a transverse electric field according to an illustrative embodiment of the invention. A sample molecule enters the channel 204 in a first fluid stream of width, $w_{in}$. The molecule 202 has a velocity of $V_f$, the fluid velocity, in the z-direction and a velocity of $v_{ep}$, the electrophoretic velocity, in the x-direction due to the electric field. As the molecule 202 travels along the length of the channel 204, it moves towards the interface 206 between the two fluids. The molecule's 202 transverse velocity will diminish as it crosses the fluid interface 206 from the low conductivity buffer 208 to the high conductivity buffer 210. As a result, the molecule 202 stays at about the fluid interface 206 where, when it reaches the end of the channel, it flows out through the target output port 212 of width, $w_{out}$.

To achieve a desired concentration factor, K, the target output port 212, at the end of the flow channel 204, has a width less than the flow channel 204, while sample output port 214 and buffer output port 216 maintain constant flow velocity. Assuming the outlet channel 212 is positioned to capture 100% of the target molecules, the ratio of inlet channel width, $w_{in}$, to the target output port 212 width gives the concentration factor of the device $$K = w_{in}/w_{out}$$

The length of the channel 204 is then determined by the electric field and the fluid velocity. In the worst-case scenario, a molecule entering at the inlet wall 220 must traverse the entire inlet width, $w_{in}$, in order to be captured at the target output port 212. The channel 204 length, L, can be determined by the distance that a molecule travels in the z-direction while traversing the inlet width, $w_{in}$.

$$L = v_f w_{in}/V_{E\ low},$$

where $v_{E\ low}$ is the electrophoretic velocity of the molecule in the low conductivity buffer.

In the ideal case, the width of the target output port 212, $w_{out}$, can be similarly determined by considering the trajectory of a molecule that enters the channel 204 at around the fluid interface 206.

$$w_{out} = v_{E\ hi} L/v_f$$

where $V_{E\ hi}$ is the electrophoretic velocity of the molecule in the high conductivity buffer.

From the above three equations, the concentration factor, K, can be reduced to the ratio of conductivities of the two buffers.

Therefore, to achieve the desired concentration factor, K, the buffers are selected based on their conductivities (σ):

$$K_{ideal} = \sigma_{hi}/\sigma_{lo}$$

Figure 3:
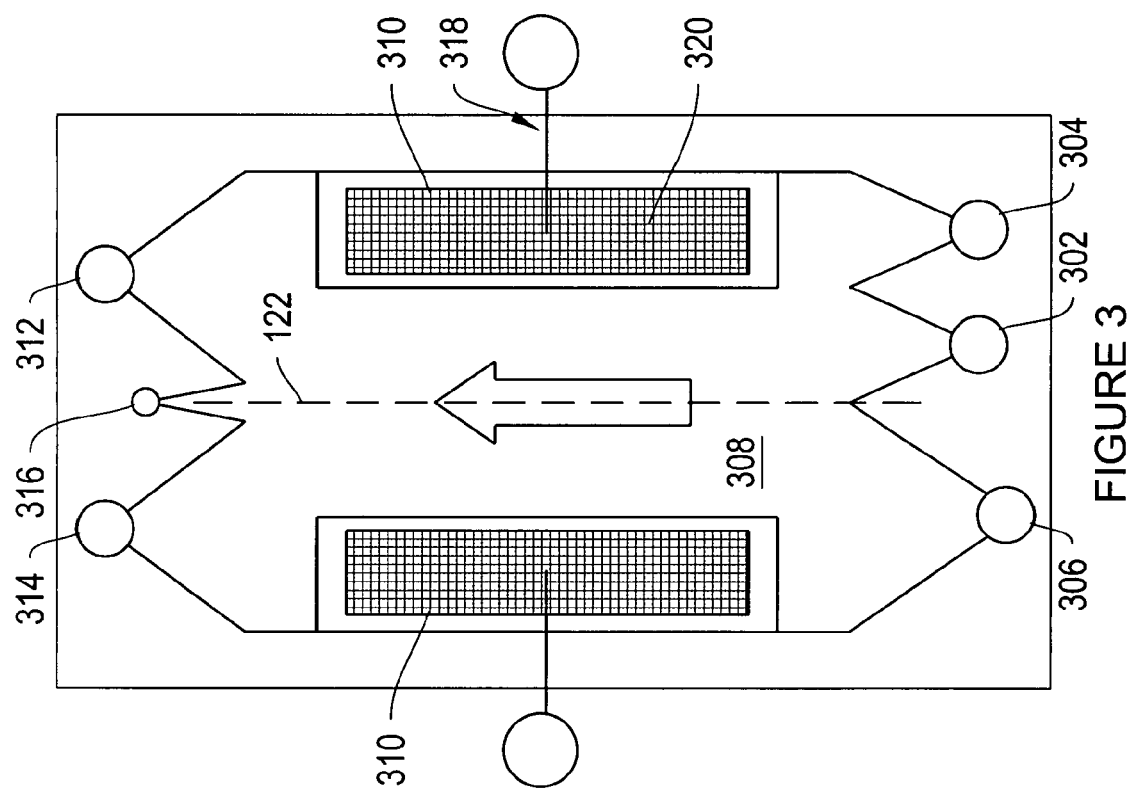
FIG. 3 is a top view of an illustrative embodiment of the device with external electrodes.

FIG. 3 depicts a top view of an illustrative embodiment of a molecule concentration device 300 with external electrodes. In the above described embodiment 100, the device was formed with integrated electrodes 108. However, a similar device can be formed without electrodes being integrated onto the same substrate as the channel. Such a device would be less expensive to manufacture and would therefore be better suited to applications where a disposable device would provide an advantage.

The device 300 includes a sample input port 302, a buffer input port 304, and a high-conductivity buffer input 306. The device 300 also includes a flow channel 308, a pair of electrode interfaces 310, a sample output port 312, a buffer output port 314, and a target output port 316.

The sample enters through the sample input port 302. The buffer fluid enters from the buffer input port 304. The combined fluid stream then flows in laminar flow with a second fluid stream introduced through the high-conductivity buffer input 306. A pair of external platinum wire electrodes 318 are wetted in buffer reservoirs 320 positioned on either side of the flow channel 308. The buffer reservoirs 320 are in fluid and electrical communication with the flow channel 308 through an ion-permeable membrane 310, such as a cast gel or porous glass. The external electrodes 318 generate an electric field transverse to the flow channel 308.

The sample output port 312 and the buffer output port 314 carry away the bulk of the first and second buffer fluid streams. The target output port 316 carries away a portion of both fluid streams containing a higher concentration of molecules than the sample.

Figure 4:
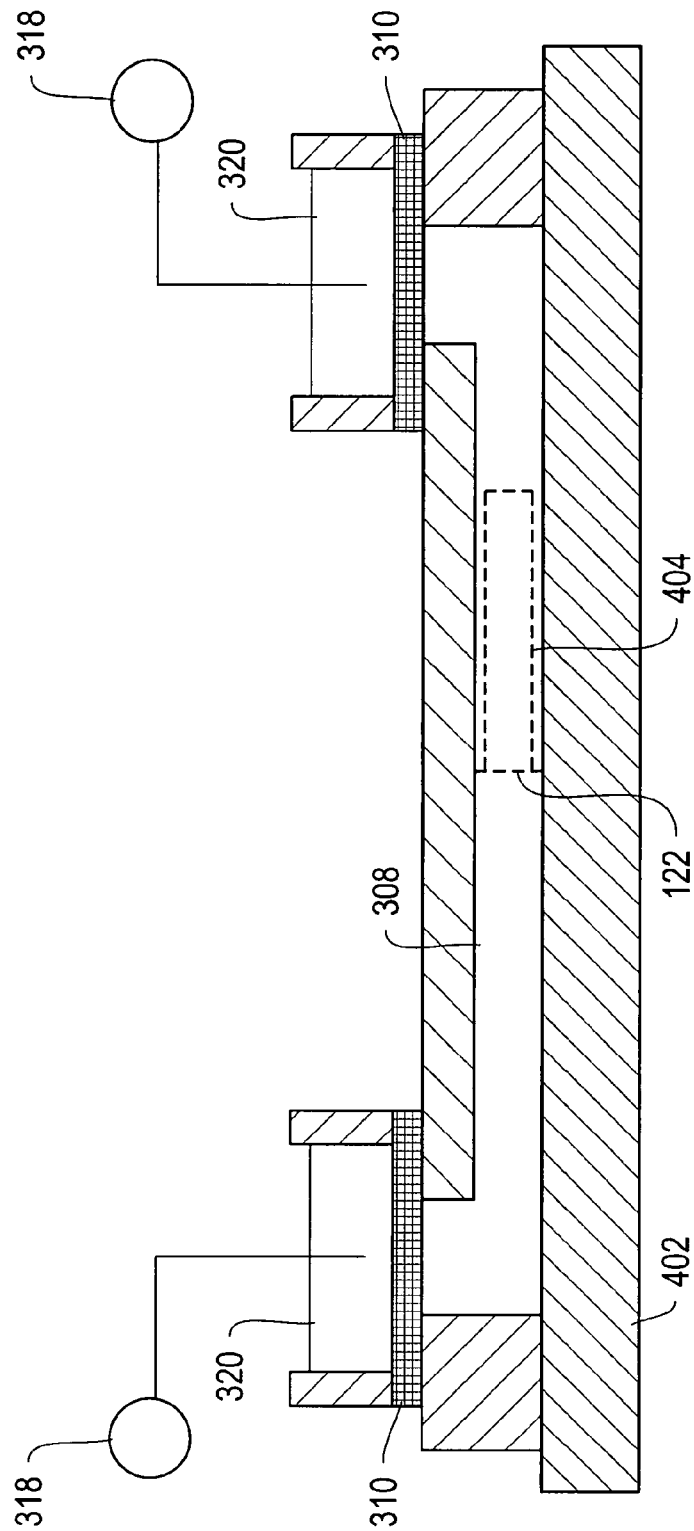
FIG. 4 is a cross-section view of the device illustrated in FIG. 3.

FIG. 4 depicts a cross-section view of FIG. 3, across the flow channel 308 at the wire electrodes 318. Visible in the cross-section view are a glass substrate 402, the flow channel 308, a pair of electrode interfaces 310, a pair of buffer reservoirs 320, and a pair of platinum wire electrodes 318. Also outlined in FIG. 4 is a sample flow region 404 within the flow channel 308, depicting the approximate position of a sample fluid flow in the flow channel in a three-input device.

While in FIG. 4 the flow channel is formed PDMS deposited on the glass substrate 402, in other embodiments the flow channel 308 and substrate 400 are formed from a single substrate, such as a parylene substrate.

Figure 5:
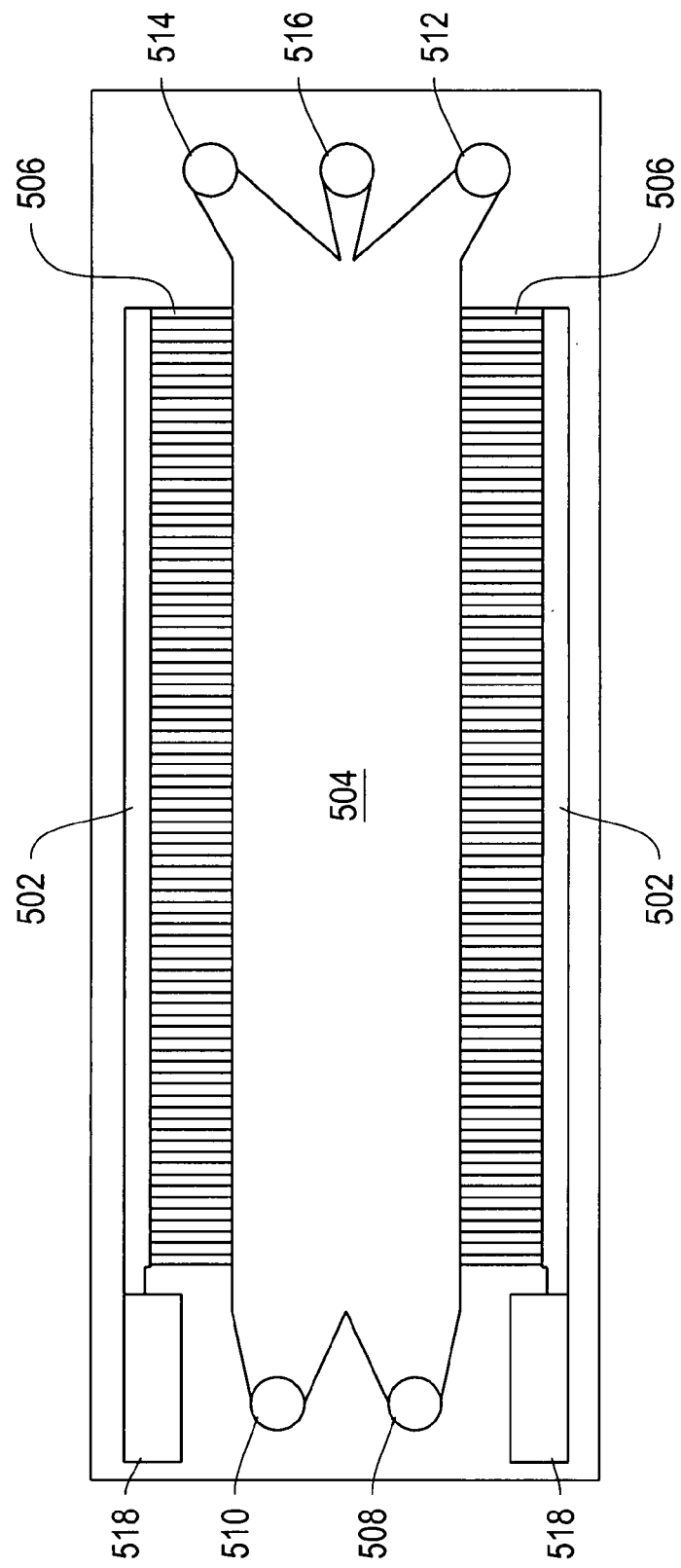
FIG. 5 is a drawing illustrating a top view of an illustrative embodiment of the device with integrated electrodes separated from the channel by ion-permeable barriers.

FIG. 5 depicts a CAD drawing illustrating a top view of an illustrative embodiment of a molecule concentration device 500, according to an illustrative embodiment of the invention. The device 500 includes a sample input port 508, a buffer input port 510, a channel 504, a pair of integrated electrodes 502, a pair of ion-permeable barriers 506, a sample output port 512, a buffer output port 514, and a target output port 516. The integrated electrodes 502 are separated from the channel 504 by the ion-permeable barriers 506.

In one embodiment, the input ports 508 and 510 are 1200 µm in diameter and 2.5 mm wide at the channel 504. The flow channel 504 is 2.3 cm long and 10 µm high. The ion-permeable barriers 506 are 1800 µm long, 6 µm wide, and composed of 420 channels along the length of the main flow channel 504. The target output channel 516 width is 250 µm. The bond pads 518 for interfacing with the integrated electrodes are 3640 µm long by 1190 µm wide. The bond pads 518 provide an interface to an external power source.

FIG. 6 is a CAD drawing illustrating a close-up view 600 of one of the ion-permeable barrier 506 of the device 500 depicted in FIG. 5, according to an illustrative embodiment of the invention. The ion-permeable barrier 506 is formed from an array of channels 604. The channels 604 create an effective barrier to separate the electrode reservoirs 606 from the flow channel 608. Preferably, the width of the channels 604 forming the ion-permeable barrier 506 is 5 µm or less.

Figure 7:
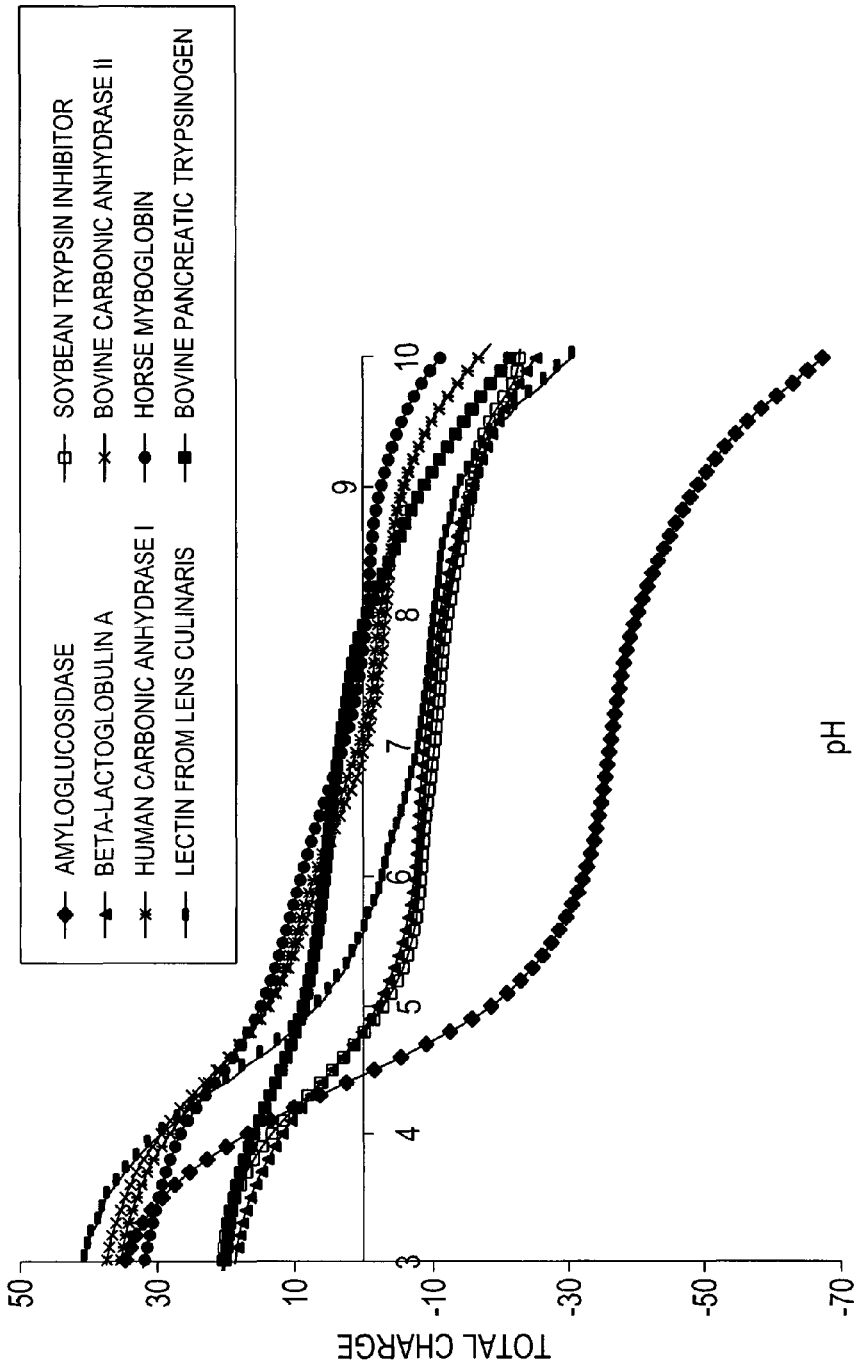
FIG. 7 depicts a set of Charge v. pH curves for an illustrative set of molecules.

FIG. 7 is a chart 700 depicting a set of Charge v. pH curves for an illustrative set of molecules. As indicated in the chart 700, the magnitude and polarity of a molecule's charge changes depending on the pH of the fluid containing the target molecule. In an illustrative embodiment of the invention, the pH of a first fluid stream can be selected such that a target molecule has a negative or positive polarity. The pH of the first fluid stream can be further selected to change the magnitude of the target molecule's charge. If the pH of the first fluid stream is selected such that the target molecule has zero charge, the target molecule is said to be at its isoelectric point. When the target molecule is at its isoelectric point, it has a low electrophoretic velocity and therefore responds weakly to the electric field across the channel.

Figure 8A:
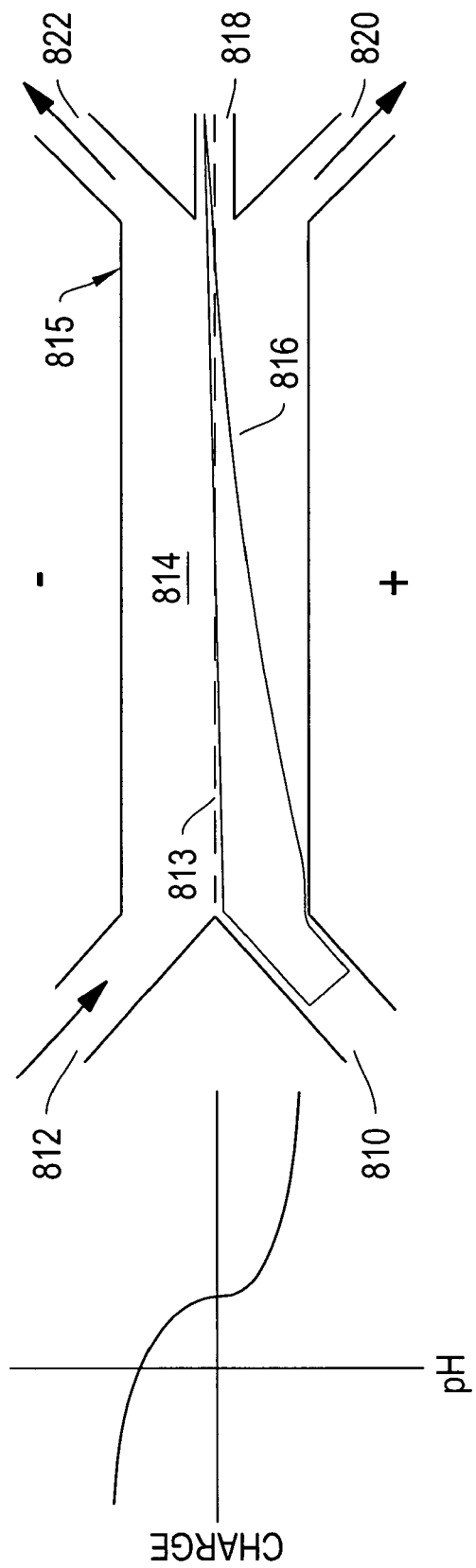
FIG. 8A is a schematic diagram of a device, according to an illustrative embodiment of the invention, to concentrate target molecules into the fluid stream collected by the target output port.

FIG. 8A depicts the operation of a device, according to the illustrative embodiment of the invention described in FIG. 1, for concentrating target molecules 816 into a fluid stream collected at the target output port 818. The depiction illustrates the illustrative embodiment of the device described in FIG. 1 performing the method described further in FIG. 8B. The depiction illustrates a sample input port 810, a buffer input port 812, a flow channel 814, a sample output port 820, a buffer output port 822, and a target output port 818.

Figure 8B:
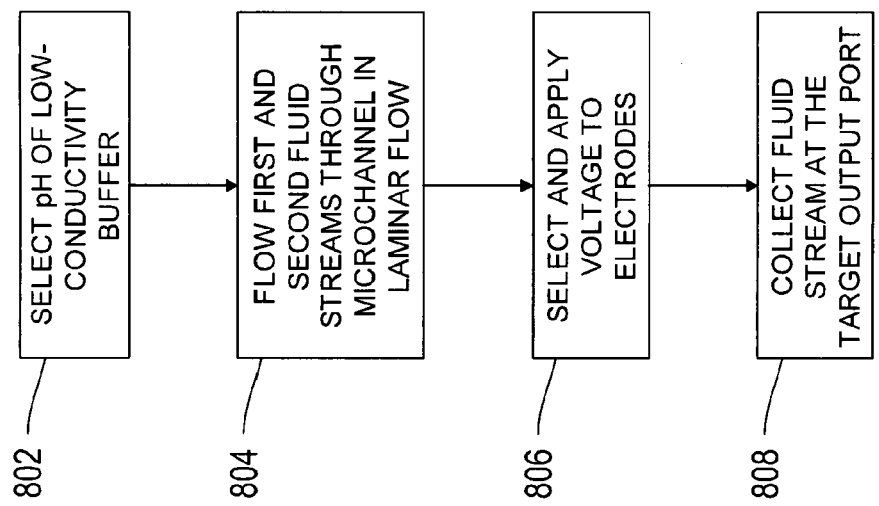
FIG. 8B is a flowchart showing a method for concentrating target molecules from a fluid stream using a microfabricated molecule concentrating device, according to an illustrative embodiment of the invention.

FIG. 8B is a flowchart showing a method for concentrating target molecules from a fluid stream using a microfabricated molecule concentrating device, according to an illustrative embodiment of the invention. The concentration process includes selecting an appropriate pH for the sample buffer (step 802), flowing two fluid streams through a channel (step 804), applying an electric field across the channel transverse to the direction of fluid flow (step 806), and collecting a fluid stream at the end of the channel consisting of a high concentration of target molecules (step 808).

More specifically, the pH of the sample buffer is selected such that the target molecules 816 will have some non-zero charge (step 802), whether positive or negative. Without some amount of charge, the target molecules 816 will have a low electrophoretic mobility and will therefore not move towards the fluid interface 813 with a sufficient electrophoretic velocity in response to the electric field. Thus, the magnitude of the charge must be above a lower limit, below which the electrophoretic velocity is insufficient to move the target molecule to the fluid interface 813 before reaching the end of the channel 814. However, the magnitude of the charge can also be too large. In that case, the electrophoretic velocity of the target molecule does not decrease sufficiently upon reaching the fluid interface 813, allowing the target molecule to continue to move towards the wall of the channel 815. These molecules would be collected by a waste outlet 822 rather than the target output port 818. The upper and lower limits will be different for different types of target molecules. Ideally, the pH of the sample buffer fluid is selected such that the electrophoretic velocity of a target molecule is large enough for the target molecule to reach the fluid interface 813 before reaching the end of the channel 814, but not so large that the molecule travels beyond the target output port 818 by the time it reaches the end of the channel 814.

Once an appropriate pH for the sample buffer is selected (step 802), two buffers are simultaneously flowed through the channel such that they establish laminar flow within the channel (step 804). The sample buffer (i.e., the buffer containing the target molecule) has a low conductivity. The other buffer has a high conductivity. Because the flows are laminar, the mixing between the two fluid streams is minimal. Absent an external force, the molecules in the first fluid stream remain largely in the first fluid stream. Once the flows are laminar, an external force is applied in the form of an electric field. The polarity and magnitude of the electric field are chosen such that the field will cause the target molecules 816 to move towards the fluid interface 813. Once the polarity and magnitude of the desired field are selected, voltage is applied to the electrodes (step 806).

As the fluid streams flow through the channel, the target molecules move laterally across the channel in response to the electric field. As they flow through the channel 814, the high-conductivity buffer and the low-conductivity buffer diffuse into each other. Therefore the conductivity of the fluid surrounding a target molecule becomes higher near the fluid interface 813. As the conductivity of the surrounding fluid becomes higher, the electric field becomes weaker and the electrophoretic velocity of the target molecule becomes slower. Therefore, around the fluid interface 813, the target molecules 816 lose velocity and begin to accumulate at about the fluid interface 813.

At the end of the channel 814, the fluid streams exit through three output ports 818 and 820 and 822. The target output port 818, positioned at about the fluid interface 813, collects portions of both fluid streams and the target molecules 816 that have accumulated at about the fluid interface 813 (step 808). The first output port 820 collects the sample buffer, which contains a substantially reduced concentration of the target molecules 816. The second output port collects the high-conductivity buffer 822. The fluid stream collected by the target output port 818 can then be collected or routed for further separation, concentration, or analysis.

Figure 9A:
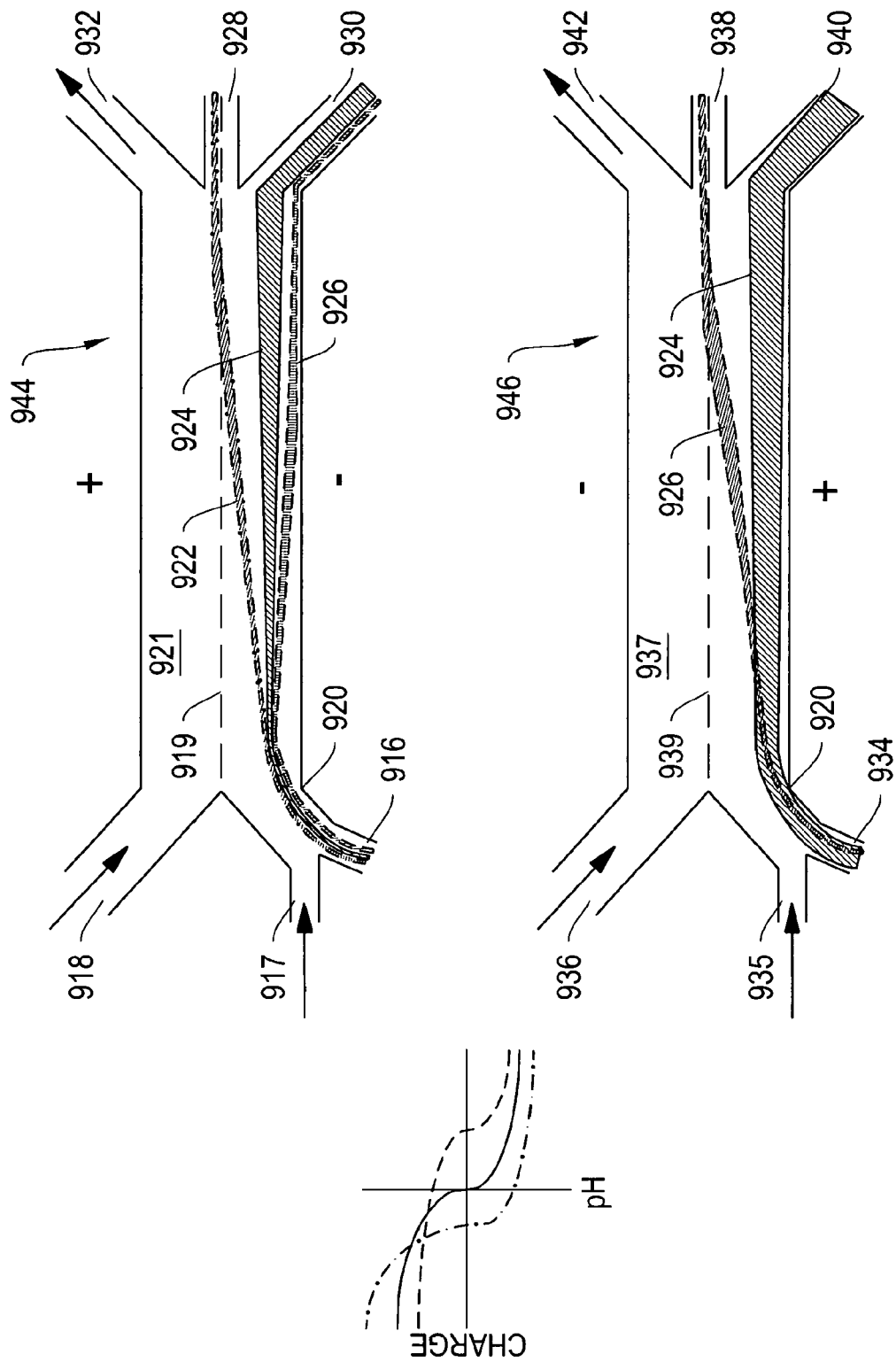
FIG. 9A is a schematic diagram illustrating the use of a device, according to an illustrative embodiment of the invention, to separate negatively charged interferents in a first stage and to separate out positively charged interferents in a second stage, such that the fluid stream collected by the first output port of the second stage contains fewer interferents.

FIG. 9A depicts the operation of a device, according to the illustrative embodiment of the invention described in FIG. 1, for separating negatively charged interferents 922 in a first stage and separating positively charged interferents 926 in a second stage, such that the fluid stream collected by the first output port 940 of the second stage contains most of the target molecules 924 in the sample fluid stream 916 but fewer of the interferents 922 and 926. The figure illustrates two devices, according to the illustrative embodiment described in FIG. 1, performing the method described further in FIG. 9B. FIG. 9A illustrates a first stage 944 and a second stage 946. The first stage 944 includes a sample input port 916, a low-conductivity buffer input port 917, a high-conductivity buffer input port 918, a flow channel 921, a sample output port 930, a high-conductivity buffer output port 932, and a target output port 928. The second stage 946 includes a sample input port 934, a low-conductivity buffer input port 935, a high-conductivity buffer input port 936, a flow channel 937, a sample output port 940, a high-conductivity buffer output port 942, and a target output port 938.

Figure 9B:
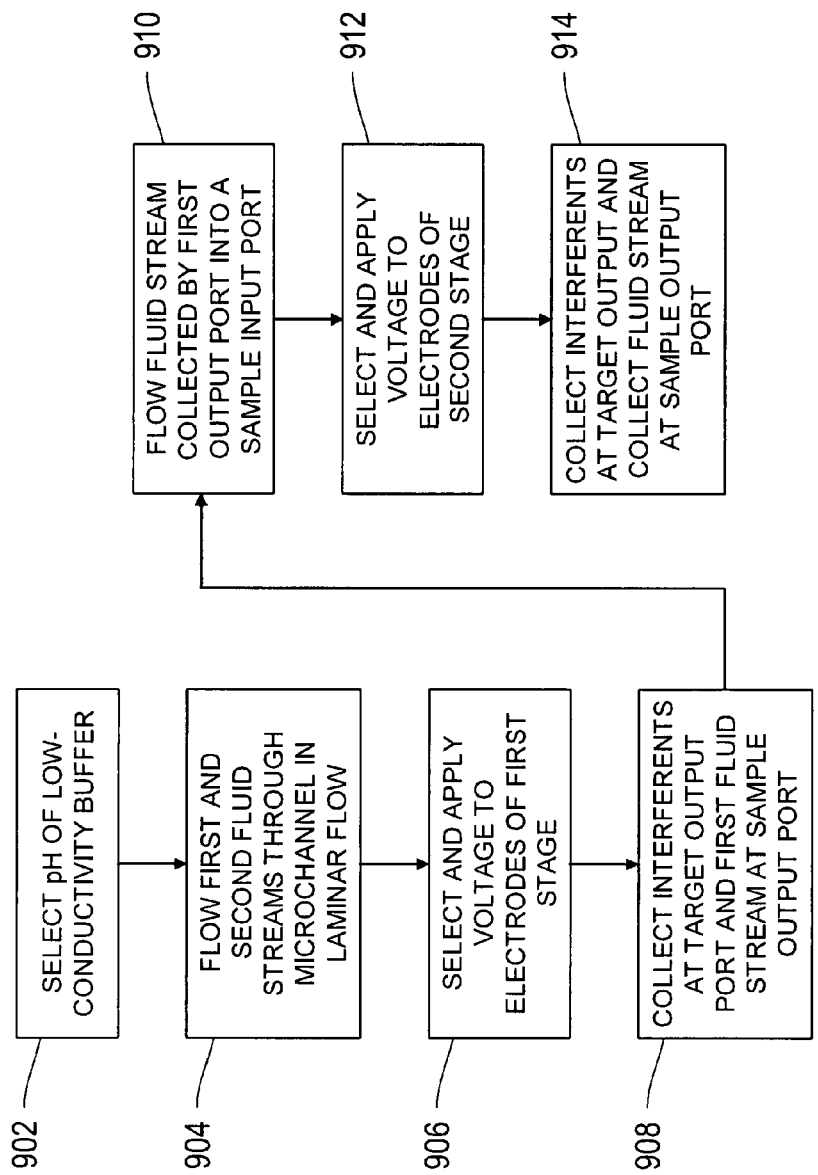
FIG. 9B is flowchart showing a method for separating other components in the sample ("interferents") from target molecules using a microfabricated molecule concentrating device, according to an illustrative embodiment of the invention.

FIG. 9B is flowchart showing a method for separating interferents from target molecules using a microfabricated molecule concentrating device, according to an illustrative embodiment of the invention. The separation process includes selecting an appropriate pH for the sample buffer (step 902), flowing two fluid streams through a channel (step 904), applying an electric field across the channel transverse to the direction of fluid flow (step 906), collecting a fluid stream at the end of the channel (step 908), flowing that fluid stream through a second stage (step 910) having an electric field of opposite polarity (step 912), and collecting a fluid stream at the end of the channel consisting of target molecules and fewer interferents (step 914).

More specifically, the pH of the sample buffer is selected (step 902) such that the target molecule is at its isoelectric point. At its isoelectric point, the target molecule has zero charge. Because the target molecules 924 have zero charge, their distribution within the first fluid stream is largely unaffected by the electric field. However, with the sample buffer at the selected pH, interferents within the sample will have a positive or negative charge.

In a first stage, two fluid streams are flowed through the channel 921 (step 904), as described for FIG. 8 above. A first polarity and magnitude are chosen for the electric field. The polarity of the electric field can be either positive or negative since, in the second stage, the polarity will be reversed and the fluid streams will be flowed through a channel 937 under the influence of the opposite electric field. Voltage is applied to the electrodes. At the end of the channel 921, the target output port 928 collects interferents of one polarity 922, while the target molecules 924 and interferents of the opposite polarity 926 are collected by the first waste outlet 930 and routed to a second stage 946.

The second stage is a second device 946, according to an illustrative embodiment of the invention. The fluid stream from the first waste outlet 930 of the first device 944 enters the sample input port 934 of the second stage 946. For the second stage, the polarity of the electric field is the opposite of the polarity of the electric field of the first device 944. Again, two fluid streams are flowed through the channel 937 of the second stage, as described for FIG. 8 above. At the end of the channel 937, the target output port 938 collects interferents of an opposite polarity 926 from the interferents collected by the target output port 928 of the first stage 944. The first waste outlet 940 collects the sample buffer containing the target molecules and fewer interferents. The second waste outlet 942 collects the high-conductivity buffer.

A continuous microfluidic protein concentrator would have applications in fieldable, rapid response instruments for clinical diagnostics, pathogen/toxin detection, and environmental monitoring. In these systems it would enhance overall sensitivity, reduce system size and make a critical contribution to the vision of automated "droplet in—answer out" instruments. These applications are not limited to liquid samples, since many strategies for air, soil, or food sampling involve first dissolving or suspending the sample in liquid before performing the analysis.

Currently sample preparation for microsensors typically involves a series of batch processes on multiple bench top instruments. In addition to reducing the size of equipment required to make a measurement, the invention offers the advantage of continuous operation, as opposed to batch processes such as centrifugation. This feature is essential for automated continuous monitoring.

A microfluidic scale is appropriate and advantageous to this design. Preliminary calculations suggest that a concentration factor of at least 20 is feasible in a 5 cm channel, and that higher factors can be readily obtained by using a series of concentrators. Sample throughput for a single concentrator 0.5 cm wide is estimated to be on the order of 30 uL/min. Therefore, an array of devices on a board measuring approximately 0.5×10×10 cm could potentially process 1 ml of sample in under 2 minutes, delivering the captured protein in a volume of less than 3 microliters.

The invention may be embodied in other specific forms without departing form the spirit or essential characteristics thereof. The foregoing embodiments are therefore to be considered in all respects illustrative, rather than limiting of the invention.

What is claimed:

1. A method for concentrating a target molecule from a fluid comprising:
   obtaining a first fluid having a first concentration of the target molecule and a first conductivity;
   selecting a second fluid, having a second conductivity, based on a relationship between the first and second conductivities, wherein the second conductivity is different from the first conductivity;
   flowing the first fluid into a channel through a first inlet;
   flowing the second fluid into the channel through a second inlet, wherein the first fluid and second fluids are in laminar flow with each other and an interface is maintained between the first and second fluids along the length of the channel;
   applying an electric field transverse to a length of the channel, whereby at least a portion of the target molecules in the first fluid are caused to migrate towards the second fluid;
   flowing a portion of the first fluid from the channel through a first outlet placed to receive the first fluid;
   flowing a portion of the second fluid from the channel through a second outlet placed to receive the second fluid; and
   continuously flowing a portion of both fluids containing a second concentration of the target molecule through a third outlet placed at about the interface between the first fluid and the second fluid, wherein the total volume of fluid flowing through the third outlet is substantially less than the volume of the first fluid flowing through the first inlet, such that the second concentration of the target molecule through the third outlet is greater than the first concentration of the target molecule.

2. The method of claim 1 where the pH of the first fluid is selected to be either higher or lower than the isoelectric point of the target molecule.

3. The method of claim 1 where the electric field applied is from about 300 to about 1000 V/cm.

4. The method of claim 1 where the first conductivity is below 20 mS/cm.

5. The method of claim 1 where the second conductivity is from about 10 to about 1000 times that of the first conductivity.

6. The method of claim 1 comprising accumulating target molecules at about the interface between the first fluid and the second fluid.

7. The method of claim 1 where the flow rate of the first fluid and the second fluid through the channel is from about 0.02 to 1 mL/min.

8. The method of claim 1 comprising determining the width of the third outlet by the following formula: (width of channel)/(2 * desired concentration factor).

9. The method of claim 1 where the solubility of the target molecule in the first fluid is substantially different from its solubility in the second fluid.

10. The method of claim 1 where the third outlet is coupled to an input port of a subsequent channel in series for further concentration such that the second concentration of the target molecule is at least 20 times greater than the first concentration of the target molecule the end of each channel.

11. A method for concentrating a target molecule comprising:
   obtaining a first fluid having a first concentration of the target molecule and a first conductivity;
   selecting a second fluid, having a second conductivity, based on a relationship between the first and second conductivities, wherein the second conductivity is different from the first conductivity;
   flowing the first fluid with the target molecule and the second fluid through a channel, wherein the first fluid and the second fluid are in laminar flow with each other and an interface is maintained between the two fluids along the length of the channel;
   selecting an electric field with an appropriate polarity and strength to cause the target molecule to accumulate at the interface between the two fluids;
   applying the electric field to the channel transverse to a length of the channel; and
   continuously collecting portions of both fluids at the interface between the two fluids at the end of the channel, wherein the total volume of fluid collected at the interface is substantially less than the total volume of the first fluid, such that the collected portions have a second concentration of the target molecule that is greater than the first concentration.

12. The method of claim 11 where the conductivity of the second fluid is from about 10 to about 1000 times that of the conductivity of the first fluid.

13. The method of claim 1, wherein selecting the second fluid based on the relationship between the first and second conductivities comprises selecting the second fluid such that a ratio between the second conductivity and the first conductivity is substantially equal to a desired concentration factor, and wherein the second concentration of the target molecule is greater than the first concentration of the target molecule by a factor substantially equal to the desired concentration factor.

14. The method of claim 11, wherein selecting the second fluid based on the relationship between the first and second conductivities comprises selecting the second fluid such that a ratio between the second conductivity and the first conductivity is substantially equal to a desired concentration factor, and wherein the second concentration of the target molecule is greater than the first concentration of the target molecule by a factor substantially equal to the desired concentration factor.

\* \* \* \* \*